United States Patent
Maurer et al.

(10) Patent No.: US 9,448,151 B2
(45) Date of Patent: Sep. 20, 2016

(54) APPARATUS AND METHOD FOR PLATELET MONITORING AND FOR ASSESSING THE QUALITY OF PLATELETS

(71) Applicant: LightIntegra Technology Inc., Vancouver (CA)

(72) Inventors: Elisabeth Maurer, Vancouver (CA); Gyasi Bourne, Vancouver (CA)

(73) Assignee: LightIntegra Technology Inc., Vancouver, BC (CA)

( * ) Notice: Subject to any disclaimer, the term of this patent is extended or adjusted under 35 U.S.C. 154(b) by 116 days.

(21) Appl. No.: 14/351,200

(22) PCT Filed: Oct. 22, 2012

(86) PCT No.: PCT/US2012/061269
§ 371 (c)(1),
(2) Date: Apr. 11, 2014

(87) PCT Pub. No.: WO2013/059770
PCT Pub. Date: Apr. 25, 2013

(65) Prior Publication Data
US 2014/0284504 A1    Sep. 25, 2014

Related U.S. Application Data

(60) Provisional application No. 61/550,376, filed on Oct. 22, 2011.

(51) Int. Cl.
| | |
|---|---|
| G01N 33/48 | (2006.01) |
| G01N 15/00 | (2006.01) |
| A61J 1/18 | (2006.01) |
| G01N 21/51 | (2006.01) |
| G01N 21/53 | (2006.01) |

(52) U.S. Cl.
CPC ............... *G01N 15/00* (2013.01); *A61J 1/18* (2013.01); *G01N 21/51* (2013.01); *G01N 21/53* (2013.01); *G01N 2015/0003* (2013.01); *G01N 2015/0084* (2013.01)

(58) Field of Classification Search
CPC ..... A61J 1/18; G01N 15/00; G01N 2015/003; G01N 21/51
USPC .......................... 250/573, 576, 564; 356/39
See application file for complete search history.

(56) References Cited

U.S. PATENT DOCUMENTS

| | | | |
|---|---|---|---|
| 4,522,494 A * | 6/1985 | Bonner | 356/39 |
| 4,657,383 A | 4/1987 | Bellhouse | |
| 4,682,887 A | 7/1987 | Bellhouse et al. | |
| 4,758,083 A | 7/1988 | Bellhouse et al. | |
| 4,830,510 A * | 5/1989 | Bellhouse | 366/219 |
| 5,750,998 A | 5/1998 | Goldman | |

FOREIGN PATENT DOCUMENTS

WO    PCT/US07/067231 A1    11/2007

OTHER PUBLICATIONS

Extended European Search Report from co-pending European Patent Application No. 12842318.3-1553/2770973.

* cited by examiner

*Primary Examiner* — Thanh Luu
(74) *Attorney, Agent, or Firm* — Hancock Hughey LLP

(57) ABSTRACT

Apparatus and methods for monitoring platelet quality are disclosed. A bag of platelet concentrate is oriented in a desired manner on a transparent surface that is illuminated from one side with a light source. A clamp applies pressure to a desired portion of the bag to temporarily manipulate a predetermined portion of the bag and therefore the fluid in the bag in a known and repeatable manner. A flow inducing member applies pressure to the bag to thereby cause a turbulent flow of the fluid from the bag through a flow path. A detector records optical characteristics of light diffracted by the flowing particles, which is analyzed by software to derive a score correlating to the quality of the platelets. Platelet swirl is scored as a measure of platelet quality where more resting, discoid platelets result in a higher score.

12 Claims, 7 Drawing Sheets

APPARATUS AND METHOD FOR PLATELET MONITORING AND FOR ASSESSING THE QUALITY OF PLATELETS

FIELD OF INVENTION

This invention relates to apparatus and methods used for medical diagnostics, and more particularly to apparatus and methods for automated monitoring platelet quality to assess and objectively determine the quality of the platelets based on observing, measuring, characterizing and quantifying platelet swirl and for assessing platelet quality based on swirl characteristics and observations.

BACKGROUND

The phenomena colloquially known as "platelet swirl" has been known and observed by clinicians for a long time. For instance, it is known that platelet swirl can be observed when platelets in a conventional or standard platelet storage bag are moved in the bag and held against a light source. Many people are looking for swirl in platelet products, but such human observation is very subjective and there is no known basis for analytically assessing or measuring platelet swirl. Nonetheless, it is known that the swirl goes away during aging or when platelets get activated by bacteria or other stress factors such as pathogen inactivation. Swirl might also be absent in a fresh platelet product due to donor factors.

When normal discoid platelets are gently rocked, they scatter the incident light in different directions. Thus, the visually apparent phenomenon known as swirling stems from the moving opalescence caused by the changing orientation of platelets relative to the incident light. When platelets have undergone shape change, which can be considered as a disk-to-sphere transformation, the platelets are said to be activated and they lose the ability to change their orientation. Pseudopods, which are protrusions from the spherical cell body caused by cell activation, do not affect the inability of the cells to demonstrate swirling. As a consequence, all activated platelets scatter light in the same direction, resulting in a dull, unchanging appearance to the sample that is visually distinguishable from swirling. Thus, discoid platelets (and also other nonspherical shapes) show the swirling effect but spherical platelets do not. The observation of platelet swirling is a simple but subjective inherently unreliable test for the nonspherical shape of platelets in concentrates, and thus a subjective assessment of platelet quality.

Although the phenomena of platelet swirl are not well understood and the physical and chemical basis for the phenomena is not well studied, swirl has been used as a quick platelet quality test for many years. Thus, clinicians have often characterized the quality of platelets based upon swirl: if the platelets demonstrate swirl when the bag is manipulated the concentrate may be deemed to be adequate for clinical uses such as transfusion. If the platelets do not swirl, the platelets have been activated and the concentrate might be discarded.

But it will be appreciated that quality determinations based on subjective observations make for a crude and unreliable quality test, especially for a valuable medical product. Nonetheless, there are no known quantifiable tests to assess platelet quality based on swirl; see, e.g., *Past and Future Approaches to Assess the Quality of Platelets for Transfusion*, Maurer-Spurej, Elisabeth, and Chipperfield, Kate, Transfusion Medicine Reviews, Vol. 21, No. 4 (October), 2007, pages 295-306.

As an illustration of current practice, visual inspection of the swirling effect might be performed before a platelet concentrate is released for transfusion, yet there is little published evidence linking the observed findings to clinical outcome. A swirling score is sometimes recorded during research studies by extensively trained research personnel but because there is no reasonably objective basis for assigning a score swirl assessments are not used routinely.

However, use of an automated and objective device for routine platelet monitoring of platelet units based on the swirling effect has so far not been particularly successful. The so-called Blood Monitoring System invented by Bellhouse (U.S. Pat. No. 4,675,019) detected light transmission changes in agitated platelet bags. However, this method only detects changes in the surface area of the cells facing the light source. Due to the very small size of platelets (2-3 micrometer diameter (see FIGS. 12 and 13), very small changes lead to highly variable results of low precision. Increasing the precision by using imaging techniques is limited by the small size of platelets, their low density which causes constant thermal movement in suspension and thus low image resolution, and the heterogeneity of platelet concentrates. As a result, no automated test is currently known to routinely measure platelet quality. Currently, the short, 5-day shelf life of platelet concentrates is largely dictated by the risk associated with bacterial contamination and not by platelet quality. With the implementation of bacterial testing and pathogen inactivation, platelet quality will become the major determinant for the shelf life of platelet concentrates. However, extended use of platelet concentrates stored beyond 5 days requires quality testing to ensure that the platelet concentrate is suitable for clinical uses such as transfusion. In addition, high platelet quality would be expected to result in improved clinical efficacy, determined by count increment, improved hemostasis, and lower risk for adverse reactions in recipients. No in vitro quality test has yet demonstrated a good correlation with clinical efficacy or improved hemostasis.

There is a pronounced need therefore for an apparatus that facilitates quantitative assessment of platelet quality, and more particularly, the phenomena of platelet swirl, as a measure of the quality of the platelets.

SUMMARY OF INVENTION

The present invention provides an apparatus and method for quantified measurement of platelet swirl in order to assess and quantify platelet quality based on quantifiable and reproducible criteria.

The invention uses apparatus to temporarily and non-invasively adjust a volume of an aliquot of platelet concentrate within a conventional platelet storage container by restricting the volume in a known, repeatable and desired manner, then inducing swirl of platelets by causing a turbulent flow in the aliquot. The turbulent flow is measured with optical measuring apparatus and the optical characteristics are recorded. Data obtained from optical measurements are analyzed in a microprocessor that uses an algorithm to determine a swirl score. If the swirl score is above a predetermined threshold value then the platelet sample is deemed to be acceptable for clinical use. If the swirl score is below the predetermined threshold then the sample is not sufficient for clinical use.

The invention facilitates repeatable swirl pattern in platelet concentrate aliquots and optical data is analyzed with the software to generate a swirl score that correlates to the quality of the platelets in the concentrate. The swirl score may be used to make reliable determinations regarding the quality and clinical usefulness of the platelets.

Computer vision and pattern recognition is well known in areas like rheology of fluid plastics. One surprising aspect of the present invention is that if platelets are discoid and capable of swirl and the turbulent flow is always initiated the same way the swirl pattern will always look the same. This constancy and reproducibility of the phenomena facilitates detect and recognition of the physical phenomena even when analysis of the sample produces a lot of optical noise.

BRIEF DESCRIPTION OF THE DRAWINGS

The invention will be better understood and its numerous objects and advantages will be apparent by reference to the following detailed description of the invention when taken in conjunction with the following drawings.

in FIG. 1 the apparatus is illustrated without a bag of platelets being present.

FIG. 8 is a top plan view of the apparatus.

FIG. 9 is an upper perspective view of the apparatus.

FIG. 10 is a side elevation view of the apparatus.

FIG. 11 is a front elevation view of the apparatus.

DETAILED DESCRIPTION OF ILLUSTRATED EMBODIMENTS

The invention relies upon temporarily adjusting the volume of a sample or aliquot of platelet concentrate in a bag of concentrate to decrease the path length of light to be transmitted through the bag and thus through the concentrate in the bag. A temporary flow chamber is established including a constricted flow path out of the temporary flow chamber, and thus the pattern of the turbulent flow. The bag is placed on and supported by a transparent surface illuminated by a light-generating source on one side, a part of its volume is restricted and a turbulent flow is induced in the volume-restricted part of the bag. An optical detector is used to detect and record fluid flow patterns as light is transmitted from the optical source and diffracted/scattered by the sample to thereby generate optical data. Software analyzes the optical data to generate a quality score—a test swirl score—which may be used as a predictive measure of platelet quality.

Those of skill in the art appreciate that the term "swirl" is often used synonymously with "turbulent flow." However, in the present invention, turbulent flow alone does not sufficiently characterize the phenomenon because activated platelets that are subjected to the same turbulent flow as non-activated platelets do not show swirl. As used herein, therefore, the term swirl should be understood to contemplate the combination of turbulent flow with the changing optical properties of cells moving in the suspension.

One preferred apparatus to adjust the volume of the platelet concentrate comprises a clamping member having a known shape. The clamp is applied to a standard bag of platelet concentrate in a desired orientation relative to the bag so that the volume is restricted in a known and repeatable manner.

Figure 1:
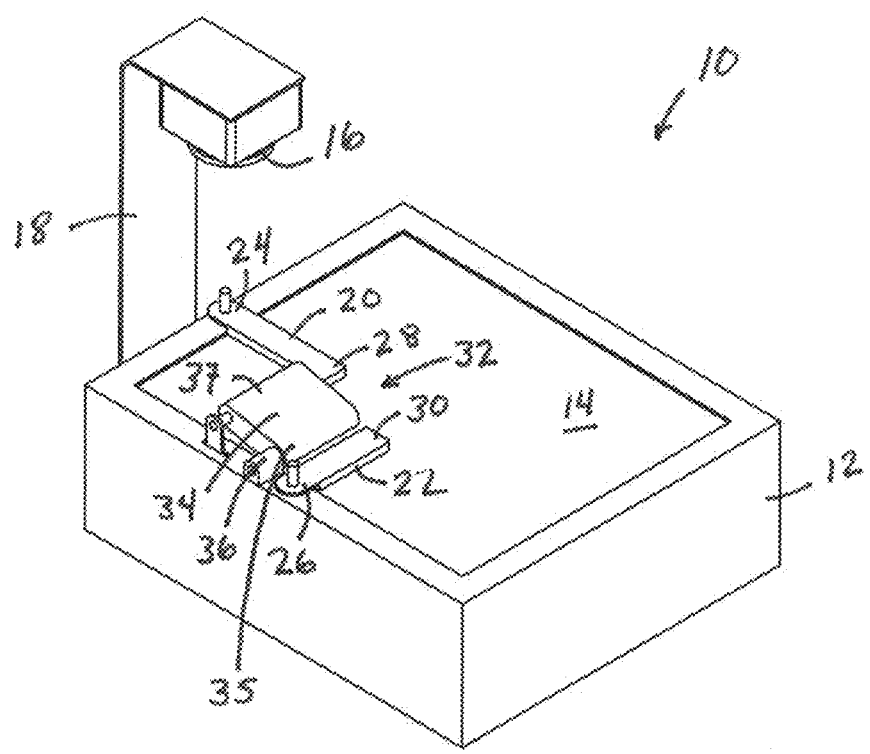
FIG. 1 is a perspective view of an apparatus according to the present invention for measuring platelet swirl.

With reference to FIG. 1, apparatus 10 comprises a housing 12 having an upper planar surface 14 comprising a glass sheet (or other translucent material through which light may be transmitted). An optical reader or camera 16 is supported a desired distance above glass sheet 14 by a support arm 18 attached to housing 12. In use, as explained in detail below, a conventional bag containing a liquid platelet concentrate is laid on glass sheet 14 for analysis. Apparatus 10 includes first and second clamp arms 20 and 22 having their first ends 24 and 26, respectively, pivotally attached to adjacent portions of the peripheral edge of housing 12. Again as detailed below, the first and second clamp arms act as volume restricting members with respect to the bag of platelets supported on glass sheet 14. Thus, when the first and second clamp arms are pivoted into an analysis position (shown in FIG. 1), the outer ends of the arms, labeled 28 and 30 in FIG. 1, are spaced apart from one another so as to define an opening 32 therebetween. Those of skill in the art will recognize that the first and second clamp arms can have various different shapes that will determine the pattern of the turbulent flow and consequently the swirl pattern when platelets are induced to move through the opening 32 and in and out of the space circumscribed by 12, 20 and 22.

Figure 2:
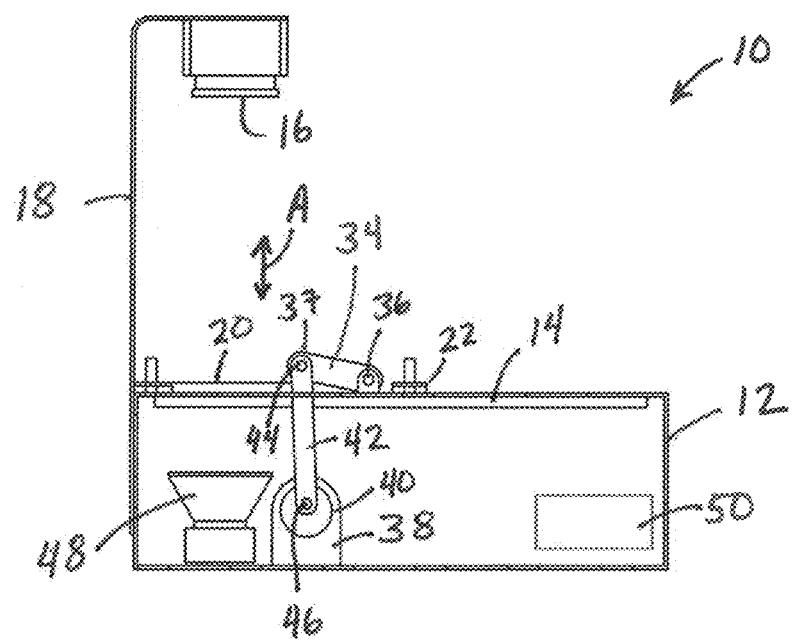
FIG. 2 is a side elevation view of the apparatus shown in FIG. 1 with the near side panel of the housing removed to illustrate select internal components of the apparatus.

With continuing reference to FIG. 1, a generally flattened paddle 34 that presents a flattened bottom surface facing the glass sheet 14 has one end 35 attached by a hinge 36 to housing 12 adjacent the attachment point of first clamp arm 20 such that the end 37 of the paddle opposite end 35 may move generally toward and away from glass sheet 14 as the paddle moves about the hinge 36. Turning to FIG. 2, arrow A illustrates the direction of movement of paddle 34 toward and away from glass sheet 14. As detailed below, movement of the paddle 34 toward glass sheet 14 applies pressure to a bag of platelets and thus induces a flow of platelets within the bag. A motor 38 in housing 12 is operable to rotate a crank wheel 40. A link arm 42 has its first end 44 attached to end 37 of the paddle 34 and its second end 46 eccentrically attached to crank wheel 40 so that rotation of crank wheel 40 by motor 38 causes end 37 of paddle 34 to move reciprocally in the direction illustrated by arrow A. The above description should be considered as one embodiment of a setup to restrict a platelet bag and induce flow in the restricted volume of the platelet bag. Instead of a horizontal orientation the apparatus could be set up vertically or at any other angle. In another embodiment the location of the detector and the light source can be switched; the components to restrict the volume of the platelet bag currently described by 12, 20 and 22 could be a separate clamp that is clipped onto the platelet bag which is then mounted onto the transparent surface 14; the paddle 34 could induce the turbulent flow by a horizontal or rotational movement.

A light source 48 is mounted in housing 12 such that light emitted from the light source is directed upwardly through glass sheet 14 and toward optical reader 16; the optical reader is positioned operatively adjacent the sample bag and the light source to detect and record the light diffracted by moving particles in the bag.

Optical reader 16, motor 38 and light source 48 are electrically interfaced with and controlled by a microprocessor 50 that is preferably a component part of apparatus 10 as illustrated. It will be appreciated that the microprocessor 50 could just as well be an external computer that is electrically connected to processing components in apparatus 10 as is known in the art. In either case, microprocessor 50 includes software for analyzing optical data generated by operation of apparatus 10 as detailed below.

Figure 3:
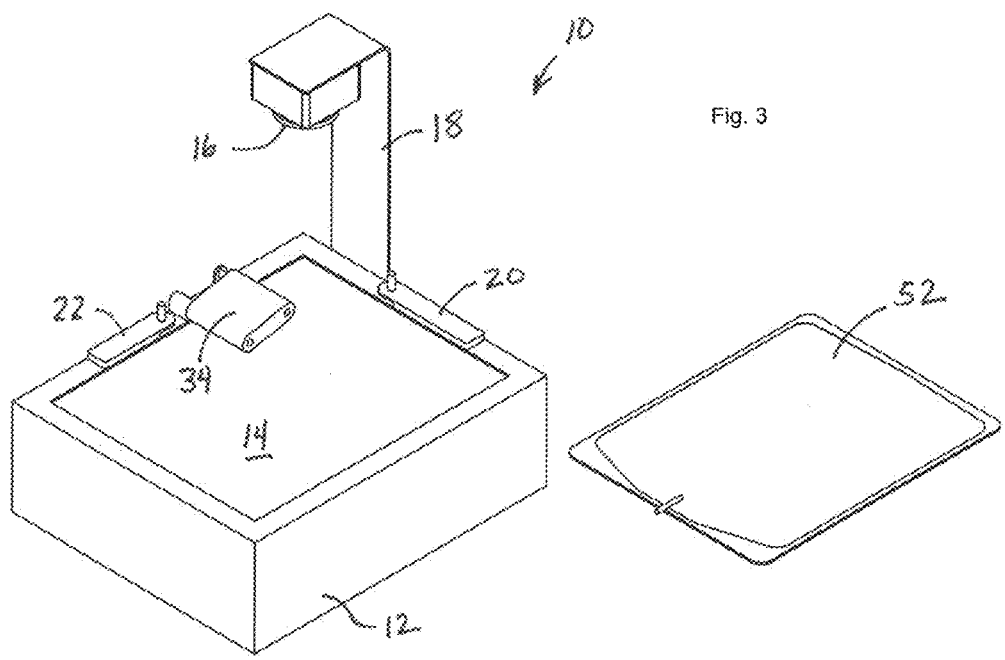
FIG. 3 is a perspective view similar to FIG. 1 and also showing a conventional storage bag for platelet concentrate, and illustrating the apparatus with its clamp arms in the open position ready to accept the platelet bag.
Figure 4:
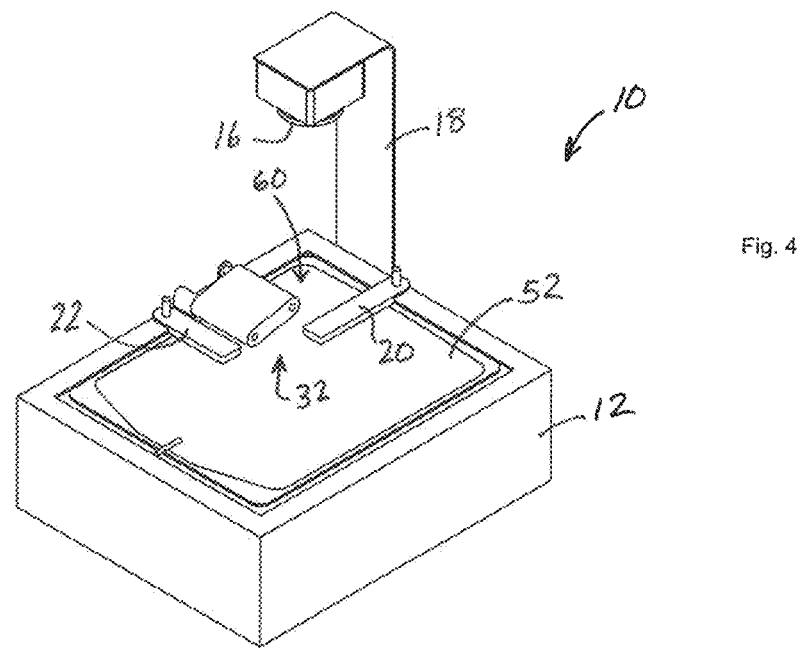
FIG. 4 is a perspective view similar to FIG. 3 except the bag of platelets has been laid on the apparatus and the clamp arms have been closed.

FIGS. 3 and 4 illustrate the positioning of the first and second clamp arms 20 and 22 relative to a platelet bag. In FIG. 3, clamp arms 20 and 22 are pivoted such that they align with the upper peripheral edges of housing 12 and are thus not interfering with ready access to glass sheet 14. A conventional bag of platelet concentrate 52 is shown to the side of apparatus 10. The bag 52 is a conventional bag for liquid platelet concentrate; the bag is translucent (or transparent—capable of transmission of light through the bag material) and flexible; it is filled with a volume of liquid platelet concentrate.

In FIG. 4 the bag 52 has been laid on glass sheet 14 with the edges of the bag roughly coincident with the edges of the glass sheet. Returning to FIG. 3, paddle 34 is shown in the "raised" position—that is, the position where end 37 is raised above glass sheet 14 by motor 38. With the clamp arms 20 and 22 in these positions and with paddle 34 in this position, the platelet bag 52 is laid on glass sheet 52 as shown in FIG. 4 with the bag 52 inserted between paddle 34 and the glass sheet. Clamp arms 20 and 22 are pivotally movable between the first position shown in FIG. 3, in which the apparatus 10 is ready for accepting a bag 52, and a second position shown in FIG. 4 in which the clamp arms are overlying the bag 52. In the second position the paddle clamp arms are exerting pressure on bag 52 and are thus performing a volume-restricting function.

To move the clamp arms from the open position of FIG. 1 to the closed position of FIG. 2, the clamp arms are rotated approximately 90° inwardly as shown so that the clamp arms overlie the bag 52—preferably the pivotal attachment between the first ends 24 and 26 of the clamp arms includes a detent so that closed positions shown in FIG. 4 may be reproduced every time the apparatus is used. In this closed position the clamp arms 20 and 22 define a general V-shape that defines the opening 32 at the apex of the V. The clamp arms are positioned on top of bag 52 and the outer ends 28 and 30 of the clamp arms are spaced from one another to define the opening 32. When they are in the closed position, the clamp arms define a partially bounded space 60 that is defined as the space inward of the clamp arms between the edges of the bag 52—the paddle 34 is positioned over the partially bounded space 60 and the opening 32 defines an opening into and out of the partially bounded space. The opening 32 thus defines a flow path from the partially bounded space to the portions of the bag outside of the partially bounded space.

Figure 5:
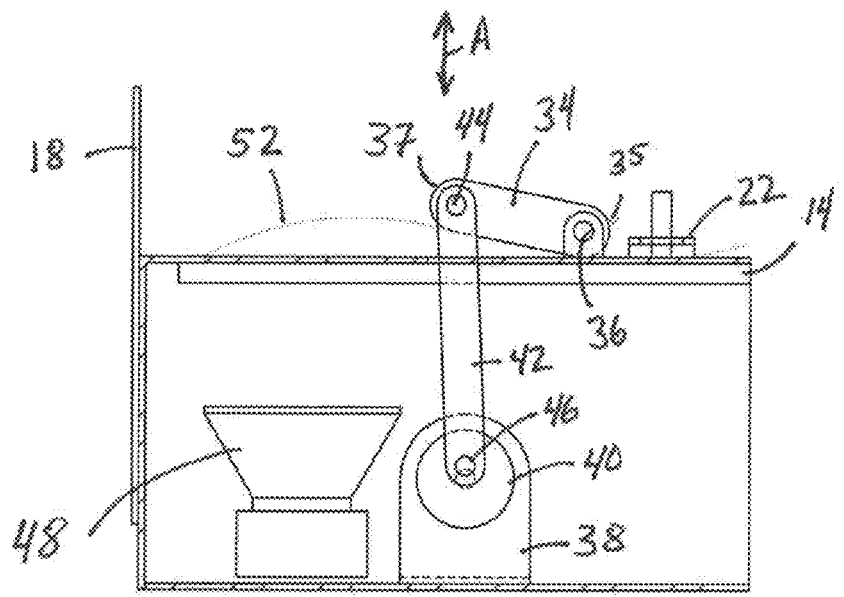
FIG. 5 is a side view of the housing of the present invention illustrating the clamps in the closed position and the flow-inducing paddle in the raised position.

Bag 52 is of course filled with a known volume of platelet concentrate—this volume is shown in FIG. 5 where the bag is somewhat expanded or inflated due to the liquid in the bag being constrained by the clamp arms 20 and 22. In essence, the bag is pinched between the clamp arms and the glass sheet 14 on which the bag is supported. With the clamp arms 20 and 22 in the closed positions, the clamp arms exert downwardly directed pressure onto bag 52 and the bag 52 in partially bounded space 60 is filled with a volume of platelet concentrate that causes the bag to be somewhat inflated, as shown. Because the volume of concentrate in bag 52 is standardized and because the position of the clamp arms 20 and 22 in the closed positions is reproduced each time the clamp arms are closed, the pressure exerted by the clamp arms produces a reproducible, reversible and standard volume-reducing function on the volume of concentrate contained in bag 52. Stated another way, every time the apparatus is used, the clamp arms exert reproduced pressure onto the bag in the same manner and thus have the same physical effect on the bag and the contents thereof. The volume of platelet concentrate in the partially bounded space 60 is always similar, with only the height varying slightly depending on the size of the bag, the final volume of platelets contained, and the actual orientation of the apparatus.

Figure 6:
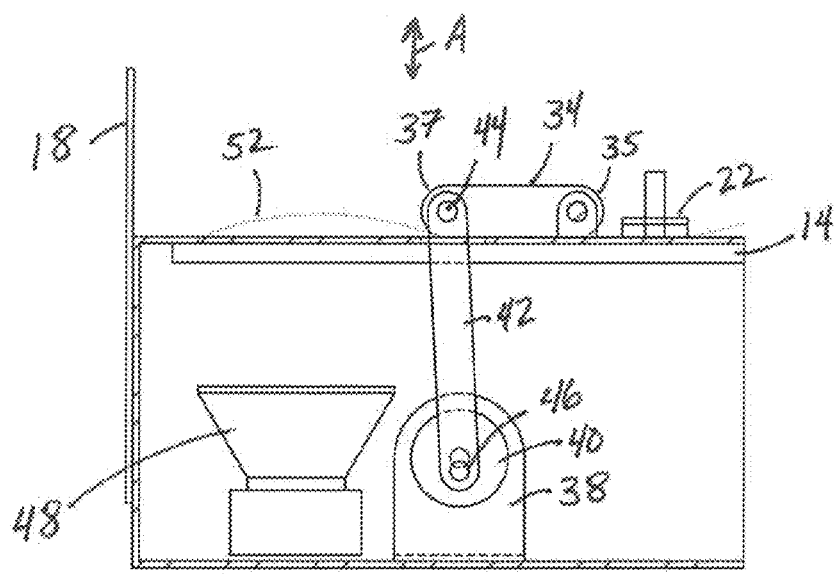
FIG. 6 is a side view similar to FIG. 5 except showing the flow-inducing paddle in its lowered position.
Figure 7:
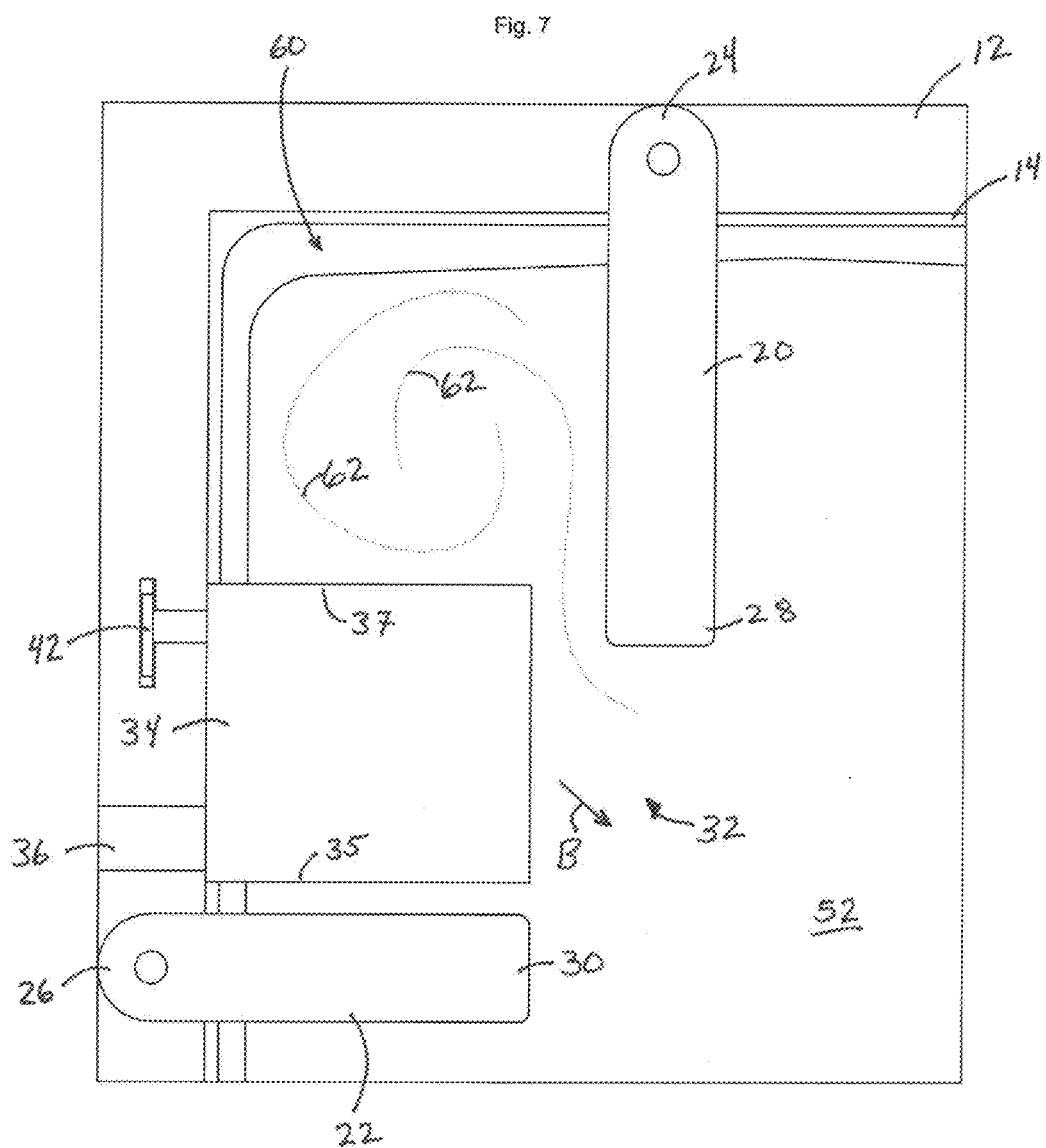
FIG. 7 is a top and partially schematic view illustrating platelet swirl as the flow-inducing paddle is moved to its lowered position.
Figure 8:
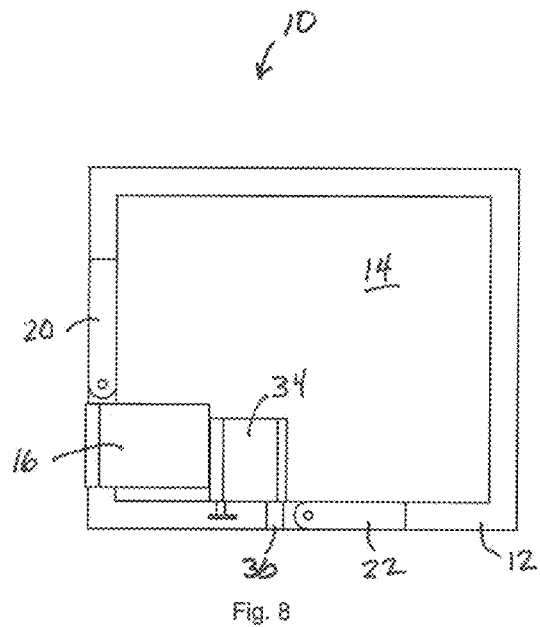
FIGS. 8 through 11 are a series of views of the apparatus illustrated in the previous figures. Specifically.
Figure 9:
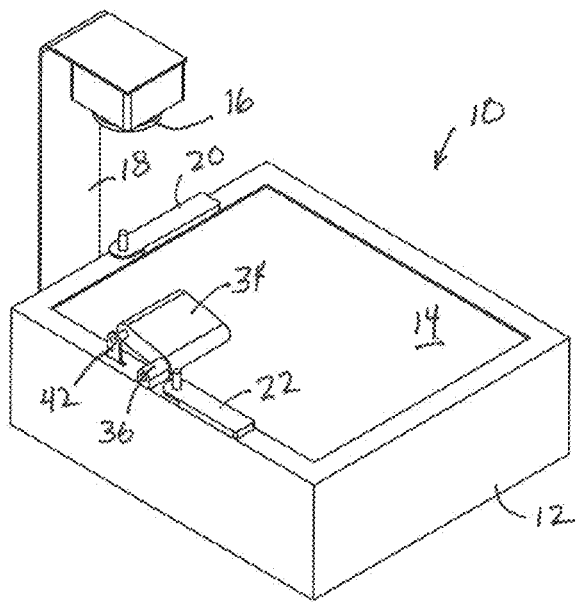
Figure 10:
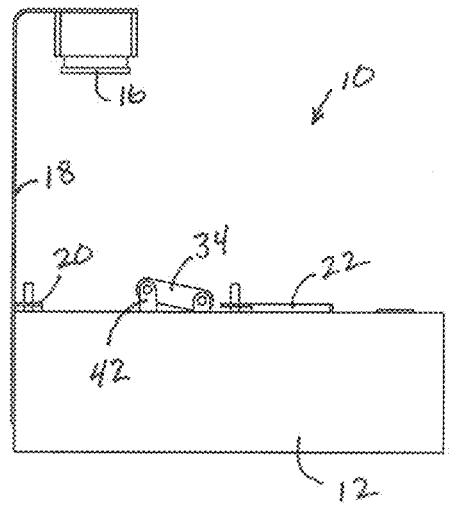
Figure 11:
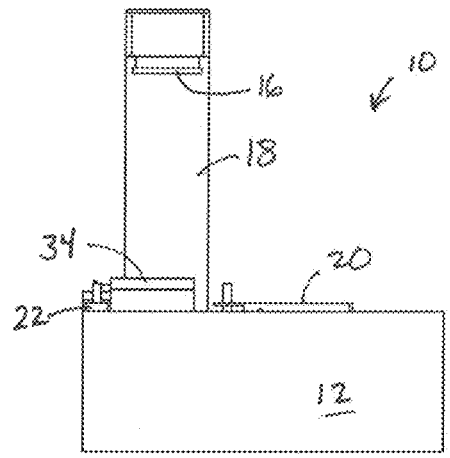
Figure 12:
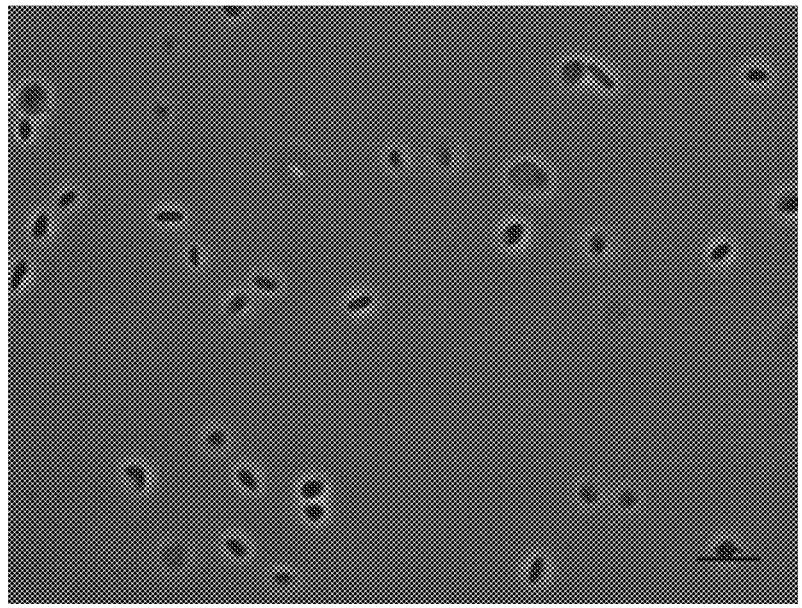
FIG. 12 is a micrograph showing platelets having a typical discoid shape that would demonstrate swirl when the concentrate is agitated.
Figure 13:
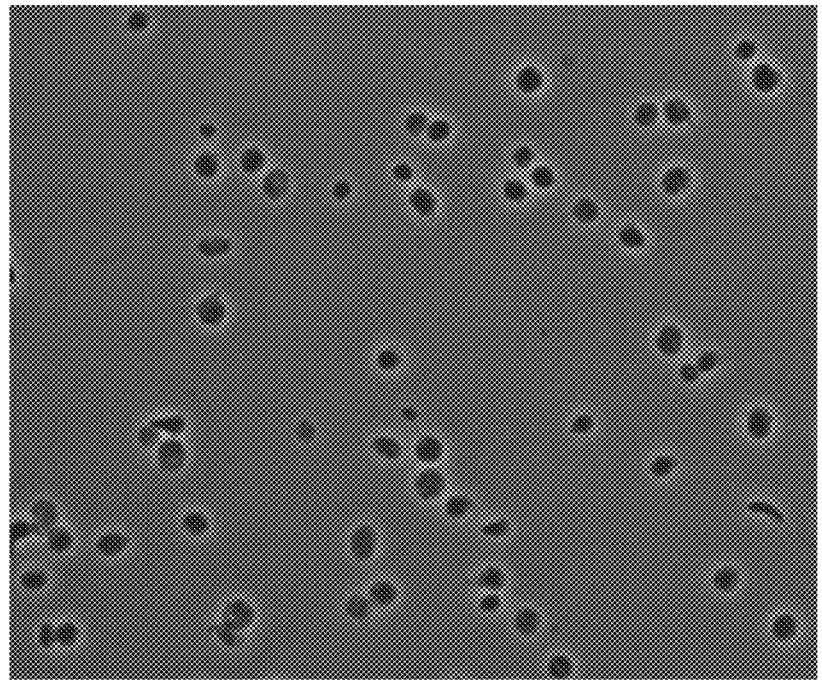
FIG. 13 is a micrograph showing platelets that have been activated and have thus undergone a discoid-to-spheroid morphological change; the platelet concentrate in FIG. 13 would not demonstrate swirl when agitated.

As noted previously, paddle 34 functions as a flow-inducing member for causing a reproducible flow of platelet concentrate within bag 52. With reference to FIG. 5, motor 38 has been operated to rotate crank wheel 40 such that the paddle 34 is in the second or lowered position. That is, the second end 37 of the paddle has been lowered toward glass sheet 14. As this happens, the paddle 34 applies pressure to the bag 52 that induces a turbulent flow of platelet concentrate in the bag, and particularly within the bounded space 60. As the paddle 34 is moved from its raised position (FIG. 5) to its lowered position (FIG. 6), the bag is compressed by the paddle. This forces the liquid platelet concentrate in the partially bounded space 60 to begin to flow. With reference to FIG. 7, the flow-inducing function of paddle 34 causes the liquid to flow from the partially bounded space 60 through opening 32 and into the portions of bag 52 that are externally located relative to the portions of bag 52 within partially bounded space 60.

The flow of platelet concentrate caused by operation of paddle 34—that is, movement of the paddle from its raised to its lowered position—is repeatable and predictable with each testing cycle. The flow of platelet concentrate is shown schematically in FIG. 7 with the concentrate flowing through opening 32. The swirl pattern that is expected with viable platelets is shown with the swirling lines labeled with reference number 62.

Operation of apparatus 10 will now be detailed.

As an initial operation, apparatus 10 is powered up with no bag 52 present on glass sheet 14. Light source 48 is illuminate and light emitted therefrom is directed through glass sheet 14 and is detected by optical reader/camera 16. The light transmission data recorded by optical reader 16 when there is no sample present (i.e., bag 52) in the apparatus comprises and is referred to herein as control value data—the optical reader functioning as a detector of light transmitted from the light source.

With clamp arms 20 and 22 in their open positions, bag 52, which is filled with a known and standard volume of liquid platelet concentrate is placed in a desired and repeatable position on glass sheet 14. More particularly, the bag 52 is positioned on glass sheet 14 with the edges of the bag coincident with the edges of the glass sheet. Positioning indicia may be included on housing 12 and/or on glass sheet 14 so that the desired position and orientation of bag 52 on apparatus is known and repeatable. Because the bag 12 is highly flexible, the rigid glass sheet 14 defines a stable support member on which the bag may reside during analysis. As noted below, in addition, the glass sheet 14 provides a stable support for the clamp arms 20 and 22, which as noted above apply pressure to the bag 52. The clamp arms 20 and 22 are then moved to their closed positions shown in FIG. 4 and in this position the bag 52 is captured or pinched between the clamp arms 20 and 22 and the glass sheet 14.

The bag 52 has a fixed and known volume within a standardized and regulated range, so pressure applied to the bag 52 by the clamp arms 20 and 22 causes a temporary restriction or displacement of the volume of platelet concentrate in the area of the bag in the partially bounded space 62 and this volume-restriction is constant and repeated with each analytical cycle. Light emitted from light source 48 is directed through glass sheet 14 and through the platelet concentrate in bag 52 in partially bounded space 60. As the light passes through the platelet concentrate the light is scattered by particles—primarily platelets in the bag. The optical data, consisting of transmitted, diffracted and scattered light, collected by optical reader 16 at this stage of the analysis comprises and is referred to herein as first test data or background data.

Motor 38 is then operated to move paddle 34 from its raised position to its lowered position to apply pressure to the bag 52 and thus induce a flow of concentrate in the bag. This causes concentrate within the bag to move from the partially bounded space 60 through opening 32 and into the portion of the bag external to the partially bounded space. As noted, the flow is somewhat turbulent.

The turbulent flow induced by the paddle 34 described above is illustrated in FIG. 7 with the swirling lines 62 as the liquid in the bag flows in the direction of arrow A through the opening 32 at the apex of the V-shape formed by the clamp arms 20 and 22.

Paddle 34 puts only slight pressure on the bag 52 and is moved only into the lowered position only briefly to induce the flow of liquid concentrate in the bag. The "self assembly" or propagation of the flow pattern 62 is monitored (similar to dropping a stone in the water and watching the ripples) and those data may be used in the analysis.

Optical reader 16, which as noted above is operatively positioned adjacent (and above) light source 48 and bag 52, records data correlating to the motion of the platelet concentrate flow that is induced by pressure applied by the paddle 34 as it applies pressure to bag 52, and the resulting scattering of light as it passes through the flowing liquid. This data comprises and is referred to herein as second test data. The microprocessor controls and synchronizes the movement of paddle 34 and the recording of platelet concentrate flow with the optical reader 16 to be precise and repeatable. Software in microprocessor 50 analyzes the data recorded by optical reader 16 in order to generate a report to the technician relating to the presence or absence of swirl, and if swirl is present, preferably a quantifiable score that is useful to the clinician as a reliable predictor of platelet quality.

More specifically, the software in microprocessor 50 analyzes optical data detected by optical reader 16 to generate a test swirl score. An analytical test cycle generates three sets of data:

a) control value data: the optical data generated by measurements taken when no bag 52 is present; control value data are used to normalize all measurement information to the same light intensity from the light source;

b) first test data: the optical data generated by measurements taken when a bag is present and the volume of the bag has been restricted by clamp arms 20 and 22 but in which no flow of liquid has been induced; this data is also known as background data;

c) second test data: the optical data generated by measurements taken when a flow of liquid has been induced by paddle 34.

The software in microprocessor 50 analyzes the three data sets just mentioned to generate a test swirl score that corresponds to the amount of swirl detected in the sample. The test swirl score is compared to reference swirl scores that are stored in a database in the microprocessor—the reference swirl scores are values that correspond to known samples that demonstrate swirl and which have been generated from test data derived from samples of platelet concentrate that demonstrate swirl. The reference swirl values define a predetermined range of swirl pattern intensity values obtained by subtracting first test data (background data) from second test data (background plus swirl pattern). By removing the background from the second test data the swirl pattern intensity will remain and be indicative of platelet quality irrespective of the storage medium (for example plasma, platelet additive solution, mixtures of plasma and platelet additive solutions) or platelet concentration.

If the test swirl score is above the predetermined threshold value or within a predetermined range of the predetermined threshold value, then the tested platelet concentrate is deemed to have a passing score. On the other hand, if the test swirl score is below the predetermined threshold value, the concentrate is judged to be inadequate for clinical use such as transfusion.

In addition to possible alternative embodiments and modifications discussed above, it will be appreciated that there are numerous equivalent structures that may be used to reduce the volume of the bag 52 and to induce a flow in the bag in known and repeatable manners. For example, a generally circular shaped clamp having an opening for fluid flow escape from within the bounded area is equivalently functional. Moreover, other methods of inducing a predictable and repeatable flow of liquid concentrate include a separate motion generator such as an arm that sweeps across the surface of bag 52 in a repeatable pattern.

It will be appreciated that in order to insure repeatability, it is important to allow flow of the sample only in a certain and repeatable way so that the swirl pattern could be predicted and the software could look just for that. This prevents random flow, which would cause random and unreliable results. The shape of the agitated volume is also important and must be known and repeatable.

FIGS. 8 through 11 are a series of views of apparatus 10 as detailed above and provide additional details about the construction and operation of the apparatus.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

The invention claimed is:

1. Apparatus for assessing the quality of platelets in a transparent container containing the platelets in a volume of fluid, comprising,
   a light source oriented relative to a transparent support such that light emitted from the light source is directed through the transparent support, said transparent support being adapted for supporting said container;
   a clamp adapted for applying pressure to a container on said transparent support, said clamp having a retaining position in which said clamp restricts a volume of fluid in said container in a partially bounded volume that has a flow path in and out of said partially bounded volume, and said clamp comprising first and second arms, each movable between a first position in which a bag may be placed on said transparent support in a desired position and the retaining position in which the first and second clamp arms pinch said bag between said clamp arms and said transparent support to thereby define the partially bounded volume;
   an optical detector positioned relative to the transparent support such that light emitted from the light source is directed to said optical detector;
   a flow inducer to apply pressure to said container in said partially bounded volume to thereby cause a turbulent flow of fluid in said partially bounded volume to flow through said flow path; and
   wherein said optical detector detects fluid flow patterns in said fluid as said fluid flows in a predictable manner through said flow path and within the partially bounded volume.

2. The apparatus according to claim 1 wherein the fluid flow pattern is detected and recorded as light is transmitted from the light source and diffracted by platelets in the fluid flowing through the flow path and within the partially bounded volume to thereby generate optical data corresponding to a detected pattern.

3. The apparatus according to claim 2 wherein the optical detector comprises a microprocessor for comparing the data corresponding to the detected pattern to data corresponding to a predicted pattern and to generate a score from the comparison, and wherein said score corresponds to platelet quality.

4. The apparatus according to claim 3 in which said score is based on pattern recognition processing in said microprocessor.

5. The apparatus according to claim 4 in which the score is predictive of platelet quality.

6. The apparatus according to claim 1 wherein each of the first and second arms has an outer end and the flow path is defined by a space between the outer ends of the respective first and second arms when they are in the retaining position.

7. The apparatus according to claim 1 wherein the flow inducer comprises a member that is movable to a first position in which said member applies pressure to said bag to thereby induce predictable flow of liquid in said bag.

8. The apparatus according to claim 7 wherein said member is movable to a second position in which said member is not applying pressure to said bag.

9. A method for assessing the quality of platelets in a transparent container containing the platelets in a volume of liquid, comprising the steps of:
   a) orienting the container in a desired position relative to a light source;
   b) restricting a known volume of liquid in the container in a partially bounded volume;
   c) while directing light from the light source through the partially bounded volume of the container, inducing a flow of liquid in the partially bounded space; and
   d) with an optical detector, detecting fluid flow patterns in the flowing liquid and recording data corresponding to the fluid flow patterns as light is transmitted from the light source and diffracted by the liquid and platelets in the container, and using pattern recognition to analyse said data and to generate a test swirl score.

10. The method according to claim 9 including the step of assessing the quality of the platelets based upon the test swirl score.

11. The method according to claim 10 wherein assessment of the quality of platelets is based upon a single test cycle comprising the step of inducing fluid flow while directing light from the light source to the optical reader to thereby generate test data.

12. The method according to claim 11 including the step of analysing predicted data and the test data to generate the test swirl score.

* * * * *